United States Patent
Sushita et al.

(10) Patent No.: US 12,419,546 B2
(45) Date of Patent: Sep. 23, 2025

(54) BLOOD FLOW AUTHENTICATION RING

(71) Applicant: BIONICS CO., LTD., Osaka (JP)

(72) Inventors: Kozo Sushita, Osaka (JP); Nobuharu Murashima, Osaka (JP)

(73) Assignee: BIONICS CO., LTD., Osaka (JP)

( * ) Notice: Subject to any disclaimer, the term of this patent is extended or adjusted under 35 U.S.C. 154(b) by 0 days.

(21) Appl. No.: 19/091,881

(22) Filed: Mar. 27, 2025

(65) Prior Publication Data

US 2025/0221635 A1 Jul. 10, 2025

Related U.S. Application Data

(63) Continuation of application No. PCT/JP2023/035496, filed on Sep. 28, 2023.

(30) Foreign Application Priority Data

Sep. 28, 2022 (JP) ................. 2022-155173

(51) Int. Cl.
*G06F 21/00* (2013.01)
*A44C 9/00* (2006.01)
(Continued)

(52) U.S. Cl.
CPC ............ *A61B 5/117* (2013.01); *A44C 9/0053* (2013.01); *A61B 5/6802* (2013.01); *G06F 21/32* (2013.01)

(58) Field of Classification Search
CPC ..... A61B 5/117; A61B 5/6802; A44C 9/0053; G06F 21/32
See application file for complete search history.

(56) References Cited

U.S. PATENT DOCUMENTS

| | | | | |
|---|---|---|---|---|
| 11,324,292 B2* | 5/2022 | Min | ..................... | A44C 9/0053 |
| 2003/0037264 A1* | 2/2003 | Ezaki | ..................... | G06F 21/32 |
| | | | | 726/21 |

(Continued)

FOREIGN PATENT DOCUMENTS

| | | |
|---|---|---|
| CN | 107006963 A | 8/2017 |
| JP | 2003-093368 A | 4/2003 |

(Continued)

OTHER PUBLICATIONS

International Search Report and Written Opinion in PCT/JP2023/035496, mailed Dec. 12, 2023, 9pp.

(Continued)

*Primary Examiner* — William A Corum, Jr.
(74) *Attorney, Agent, or Firm* — HAUPTMAN HAM, LLP

(57) ABSTRACT

Provided is a blood flow authentication ring that can achieve focus in a captured image regardless of finger size, can prevent reduction of contrast due to external light, or simplifies personal registration. A blood flow authentication ring in an embodiment of the present invention is a blood flow authentication ring having a ring-shaped cover member to be worn on a finger and configured to perform authentication with finger blood flow. The cover member at least includes an irradiation device to irradiate the finger with light and an imaging device to capture an image of light transmitted through the finger. An adjusting member is provided between an inner circumference of the cover member and the finger. The adjusting member has a function of at least one of a size compensation member and a low reflection member.

8 Claims, 15 Drawing Sheets

(51) Int. Cl.
     *A61B 5/00*          (2006.01)
     *A61B 5/117*        (2016.01)
     *G06F 21/32*        (2013.01)

(56)             References Cited

U.S. PATENT DOCUMENTS

| | | |
|---|---|---|
| 2015/0220109 A1 | 8/2015 | Von Badinski et al. |
| 2016/0034742 A1 | 2/2016 | Kim et al. |
| 2020/0085360 A1 | 3/2020 | Yuan et al. |
| 2020/0391696 A1 | 12/2020 | Kato et al. |
| 2021/0169345 A1* | 6/2021 | Wasson ............. G01N 21/3577 |
| 2024/0090835 A1* | 3/2024 | Watanabe ............ A61B 5/6826 |
| 2024/0377316 A1* | 11/2024 | Connor .................. G06V 20/20 |
| 2024/0398259 A1* | 12/2024 | Shavit ................. A61B 5/0507 |

FOREIGN PATENT DOCUMENTS

| | | |
|---|---|---|
| JP | 4432539 B2 | 3/2010 |
| JP | 2016-033815 A | 3/2016 |
| JP | 2017-506376 A | 3/2017 |
| JP | 2019-151997 A | 9/2019 |
| KR | 10-2016-0088637 A | 7/2016 |

OTHER PUBLICATIONS

Notification prior to Examination in IL application No. 319876, dated Mar. 27, 2025, 4pp.
Office Action in KR application No. 10-2025-7013731, dated Jun. 19, 2025, 10pp.

* cited by examiner

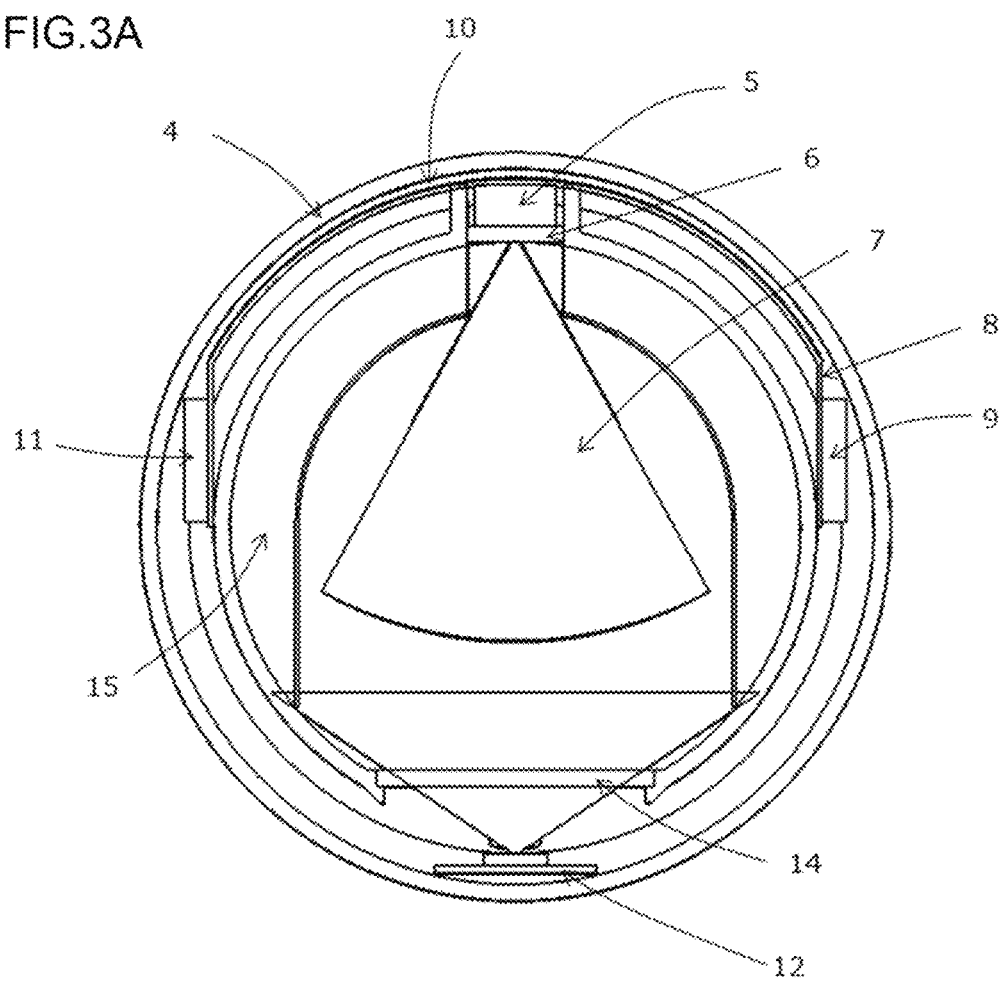

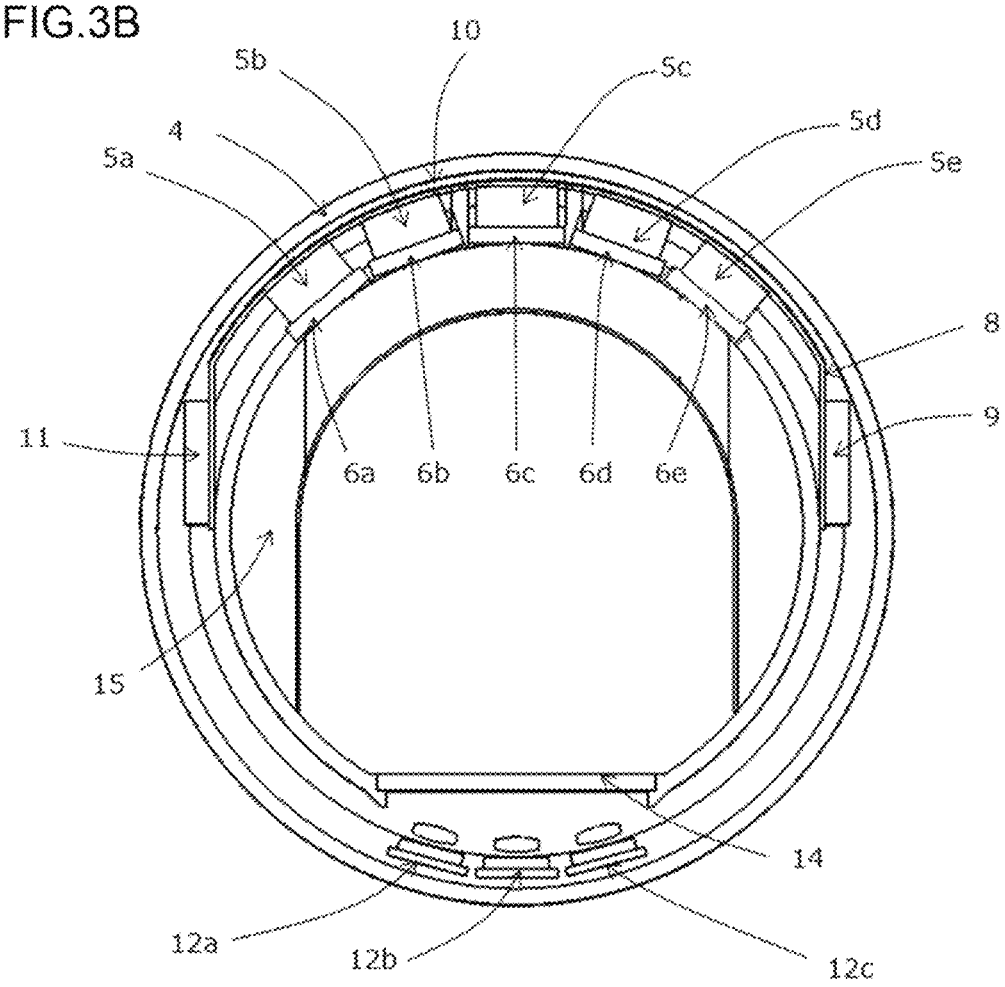

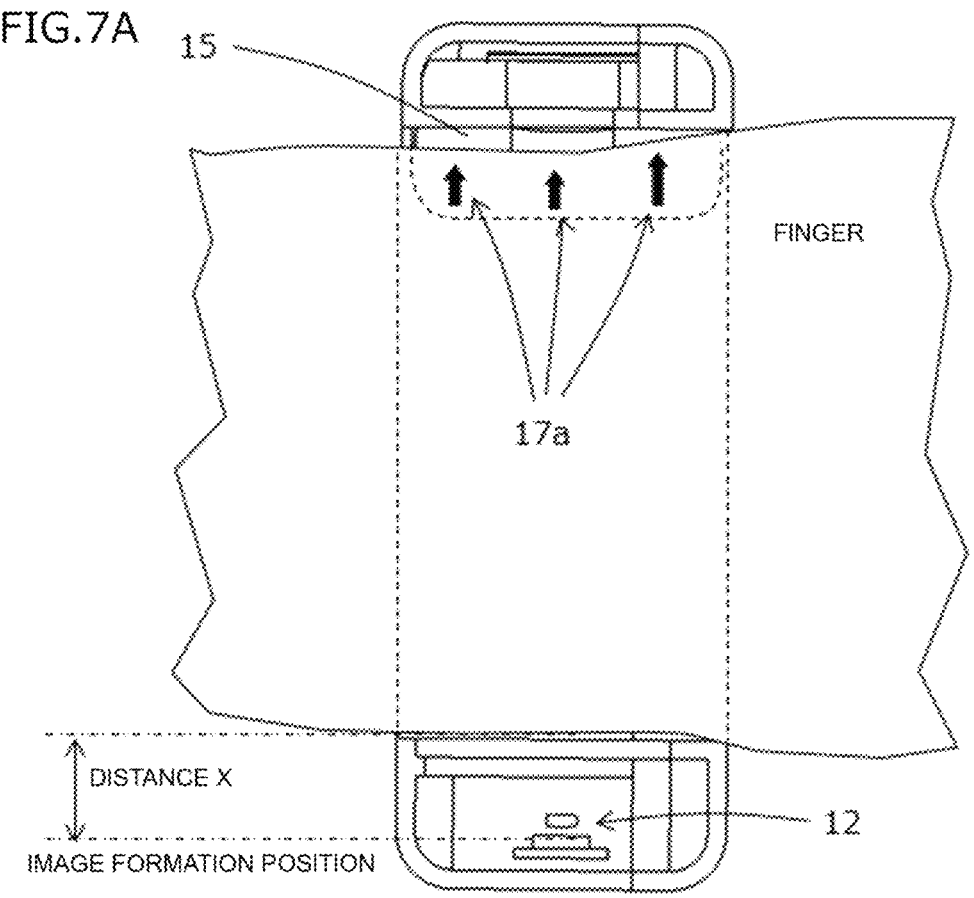

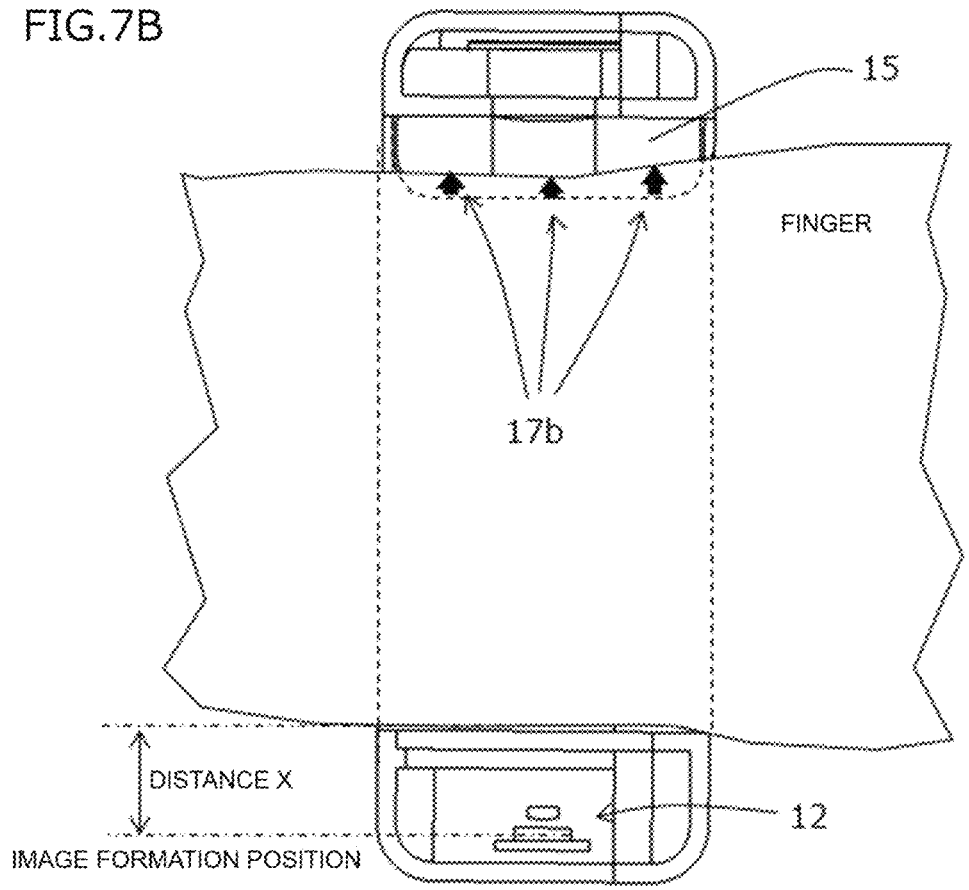

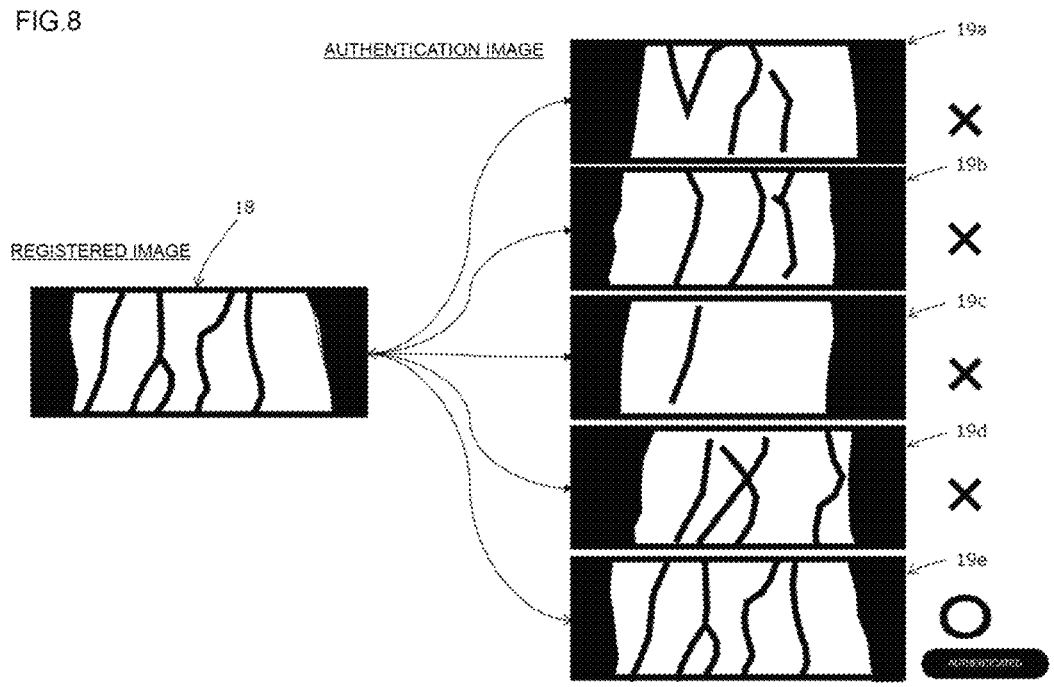

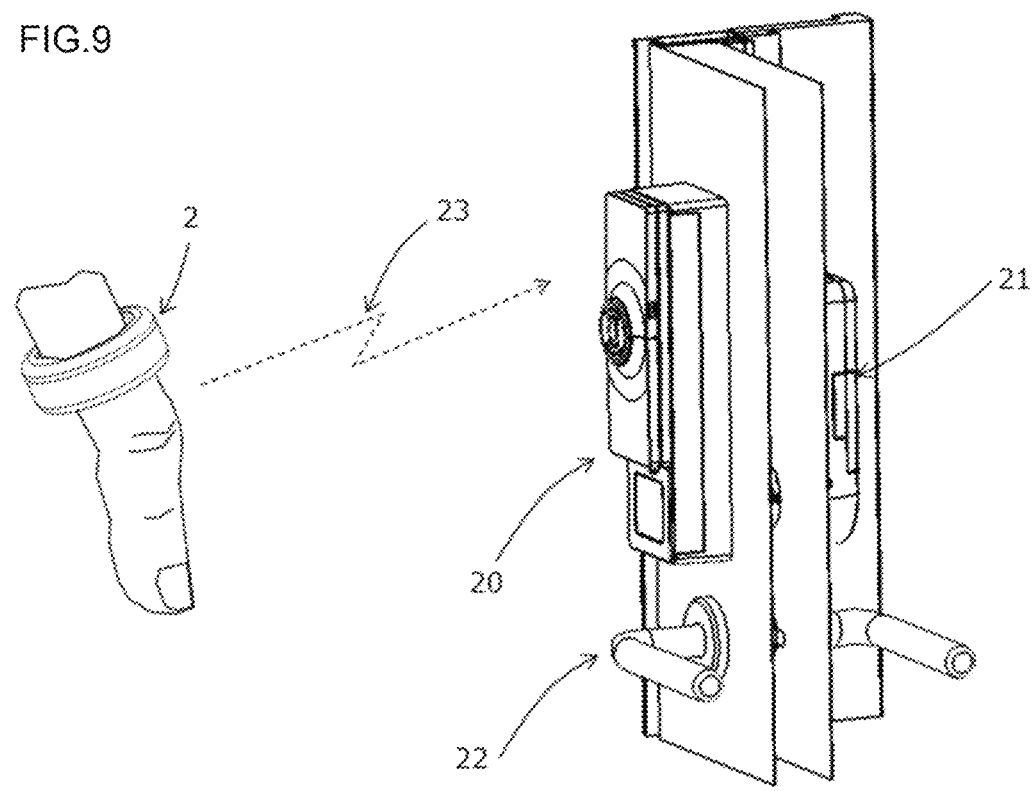

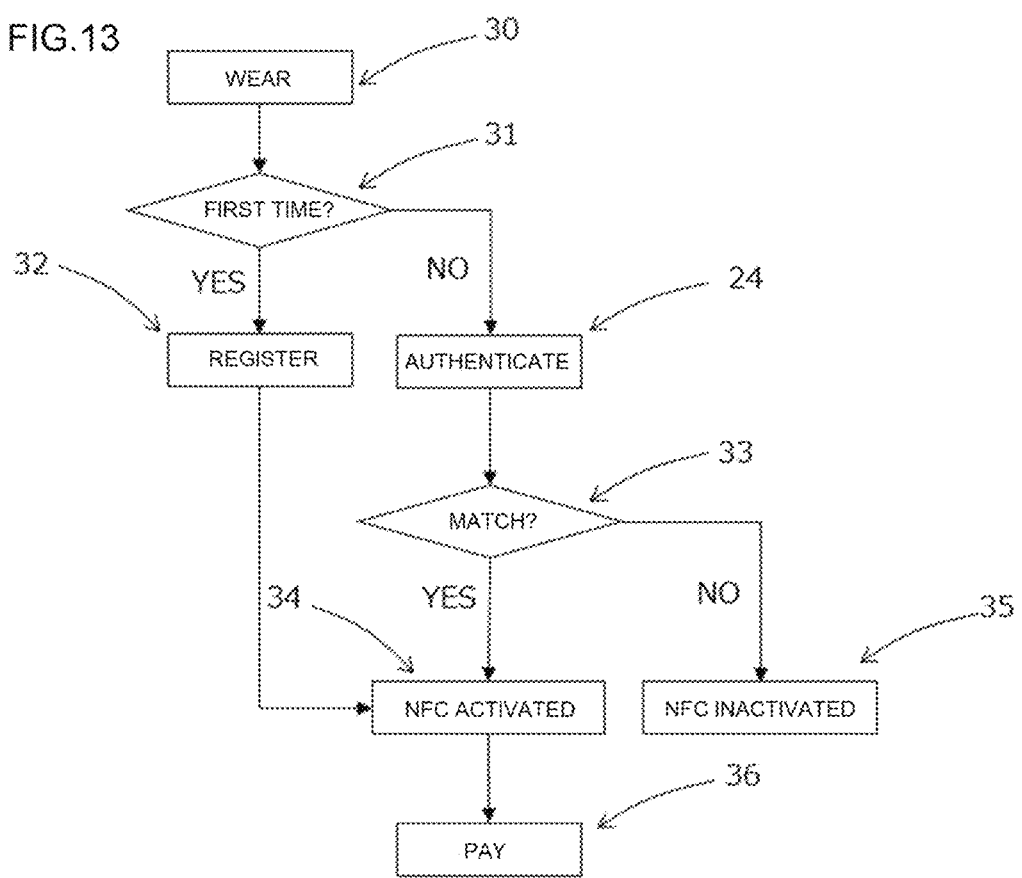

BLOOD FLOW AUTHENTICATION RING

RELATED APPLICATIONS

The present application is a continuation application of International Application No. PCT/JP2023/035496 filed Sep. 28, 2023, which claim priority to Japanese Application No. 2022-155173, filed Sep. 28, 2022, the disclosures of which applications are hereby incorporated by reference herein in their entirety.

FIELD

The present invention relates to a blood flow authentication ring that incorporates a blood flow imaging function in a finger ring-shaped ring member and performs blood flow imaging and personal authentication while being worn on the finger.

BACKGROUND

In recent years, systems that use biometric information to perform personal authentication have become increasingly popular. A method that uses a blood flow reader ring to read blood flow has been proposed as a method of personal authentication using biometric information.

CITATION LIST

Patent Literature

Patent Literature 1: Japanese Unexamined Patent Application Publication No. 2003-093368
Patent Literature 2: Japanese Patent No. 4432539

SUMMARY

Technical Problem

The blood flow reader rings in Patent Literatures 1 and 2 are disadvantageous in that the distance from an imaging surface to a subject (finger surface on which blood flow is projected) varies due to differences in the size of the finger, resulting in out-of-focus images. Patent Literatures 1 and 2 employ a method of emitting infrared light or the like and capturing an image of the reflected light. This method, however, has disadvantages in that the infrared irradiation light is reflected on the inner circumference of the ring and stray light caused by external light is reflected on the inner circumference of the ring, causing a background image to become brighter and the contrast of blood flow to decrease. Moreover, the owners of the blood flow reader rings must register themselves before blood flow authentication. In order to register themselves, they need to perform a series of registration operations, for example, by pressing a button on the blood flow reader ring, but the registration operations are complicated and the placement of the button for registration restricts the ring size, among other issues.

An object of the present invention is to provide a blood flow authentication ring that can achieve focus in a captured image regardless of finger sizes, can prevent reduction of contrast due to external light, or simplifies personal registration.

Solution to Problem

A blood flow authentication ring according to a first aspect of the present invention is configured to perform authentication with finger blood flow. The blood flow authentication ring configured to perform authentication with finger blood flow, the blood flow authentication ring comprising a ring-shaped cover member to be worn on a finger.

The cover member at least comprises an irradiation device configured to irradiate the finger with light, and an imaging device configured to capture an image of light transmitted through the finger, the irradiation device is opposite the imaging device and is placed on the back side of the finger, an adjusting member is provided between an inner circumference of the cover member and the finger.

The adjusting member has a function of at least one of a size compensation member and a low reflection member, the adjusting member is disposed at least between an inner circumference side of the cover member, and the back side and both side surfaces of the finger, and the low reflection member has a reflectivity of less than 10%.

According to a second aspect of the present invention, in the blood flow authentication ring according to the first aspect, the adjusting member has a surface with a coefficient of kinetic friction of less than 0.2.

According to a third aspect of the present invention, in the blood flow authentication ring according to the first aspect, the cover member has a solar panel.

According to a fourth aspect of the present invention, in the blood flow authentication ring according to the first aspect, light emitted by the irradiation device is at least one of near-infrared light and red light.

According to a fifth aspect of the present invention, in the blood flow authentication ring according to the first aspect, the adjusting member is an elastic member.

According to an sixth aspect of the present invention, in the blood flow authentication ring according to the first aspect, the adjusting member has a light-transmitting portion that allows light emitted from the irradiation device to pass through.

According to a seventh aspect of the present invention, in the blood flow authentication ring according to the first aspect, at least one of the irradiation device and the imaging device is provided in plurality.

A blood flow authentication ring according to a eighth aspect of the present invention is configured to perform authentication with finger blood flow. The blood flow authentication ring configured to perform authentication with finger blood flow, the blood flow authentication ring comprising a ring-shaped cover member to be worn on a finger, wherein the cover member at least comprises an irradiation device configured to irradiate the finger with light, and an imaging device configured to capture an image of light transmitted through the finger, the irradiation device is opposite the imaging device and is placed on the back side of the finger, an adjusting member is provided between an inner circumference of the cover member and the finger, the adjusting member has a function of at least one of a size compensation member and a low reflection member, the adjusting member is disposed at least between an inner circumference side of the cover member, and the back side and both side surfaces of the finger, and the low reflection member has a reflectivity of less than 10% the cover member further comprises a finger detector configured to detect wearing on the finger, and the finger detector has a registration function to automatically register a person, to be authenticated, corresponding to the finger when the finger detector detects wearing on the finger for a first time.

In the blood flow authentication ring according to the first aspect of the present invention, the adjusting member is provided between the inner circumference of the cover member and the finger, the adjusting member has a function of at least one of a size compensation member and a low reflection member, and the adjusting member is disposed at least between the inner circumference side of the cover member and the back side of the finger. Thus, the size compensation member serves as a spacer in the space between the cover member and the finger, so that focus can be achieved in a captured image regardless of the size of the finger, and reduction of contrast due to external light can be prevented, or personal authentication can be performed reliably and personal registration is simplified. The function of the low reflection member reliably eliminates the reduction in contrast of blood flow, which would otherwise be caused by stray light from external light reflected on the inner circumference side of the ring and brightening a background image.

And in the blood flow authentication ring according to the fifth aspect of the present invention, the adjusting member has a function of a low reflection member, and the low reflection member has a reflectivity of less than 10%. For example, the low reflection member may employ a sheet-like material with a reflectivity of less than 10% for 850 nm to 950 nm as a surface member. In this case, since the adjusting member has a surface with low reflectivity, the reflection on the inner circumference side of the ring due to stray light from near-infrared light irradiation or external light is also suppressed, resulting in a blood flow image with high contrast. The same effect can be achieved by applying the same low reflection treatment to the inside of the cover member even in a case where the size compensation member is not used.

And in the blood flow authentication ring according to the sixth aspect of the present invention, the adjusting member has the size compensation member to serve as a spacer in the space between the cover member and the finger, at least between the inner circumference side of the cover member and the back side and both side surfaces of the finger, so that focus can be achieved in a captured image regardless of the size of the finger, and reduction of contrast due to external light can be prevented. The function of the low reflection member reliably eliminates the reduction in contrast of blood flow, which would otherwise be caused by stray light from external light reflected on the inner circumference side of the ring and brightening a background image.

In the blood flow authentication ring according to the second aspect of the present invention, the surface of the adjusting member has a coefficient of kinetic friction of less than 0.2 and is surface-treated, which reduces snagging during finger insertion and enables smooth insertion and removal. Furthermore, increasing the slidability of the surface of the surface member enhances the durability against repeated insertion and removal.

In the blood flow authentication ring according to the third aspect of the present invention, the cover member has a solar panel so that power generated by the solar panel can be used and the solar panel can be used to charge a capacitor, storage battery, or the like. Thus, a blood flow authentication ring that does not require a power source can be provided. In a case where external power is supplied to charge the storage battery, the solar panel can be eliminated.

In the blood flow authentication ring according to the fourth aspect of the present invention, at least one of near-infrared light and red light is used.

Since red wavelengths as well as near-infrared wavelengths are easily absorbed by blood flow, near-infrared light or red light is not detected only from an area with blood flow in the captured image.

Thus, an image of blood flow can be captured with high accuracy. Since near-infrared and red light can be emitted by LEDs, for example, a near-infrared LED or a red LED can be employed as the irradiation device.

In the blood flow authentication ring according to the fifth aspect of the present invention, since the adjusting member is an elastic member, the elastic member has the amount of deformation changing according to the thickness of the finger. Thus, the elasticity of the size compensation member enables the ring to be worn with no gap while absorbing the difference in the thickness of the finger, and biases the finger in a direction from the back side to the ball side (a direction from the irradiation device toward the imaging device, downward). This configuration keeps a constant distance X from the imaging position of a camera module to the surface of the finger, regardless of the size of the finger.

In the blood flow authentication ring according to the sixth aspect of the present invention, the adjusting member has a light-transmitting portion that allows light emitted from the irradiation device to pass through. A through hole is provided in the adjusting member, for example, in a portion corresponding to the LED arrangement position in the size compensation member, so that the irradiation light (irradiation light beam) from the LED passes through the through hole and appropriately irradiates the inner circumference side of the size compensation member. In other words, with the light-transmitting portion provided in the adjusting member to allow the light emitted from the irradiation device to pass through, the effect of the adjusting member according to the first aspect is achieved, and in addition, blocking of the irradiation light (irradiation light beam) from the LED is reliably prevented.

In the blood flow authentication ring according to the seventh aspect of the invention, at least one of the irradiation device and the imaging device is provided in plurality. For example, a plurality of LEDs can be disposed to increase the quantity of light and expand the irradiation range. A plurality of camera modules can be provided to enable imaging in a wide range. LEDs with different specifications may be combined. For example, a combination of at least one red LED and near-infrared LED can be used to obtain a clearer blood flow image.

In the blood flow authentication ring according to the eighth aspect of the present invention, in addition to the effects of the first aspect of the blood flow authentication ring, the cover member further includes the finger detector configured to detect the wearing of the ring on the finger, and the finger detector has the registration function to automatically register a person, to be authenticated, corresponding to the finger when the finger detector detects the wearing of the ring on the finger for the first time. This configuration can detect the first wearing of the ring on the finger and automatically perform personal registration. Further, a blood flow authentication ring that can be easily operated without special manipulation and without restrictions on ring size can be provided. Thus, a blood flow authentication ring with simple personal registration can be provided.

BRIEF DESCRIPTION OF DRAWINGS

FIG. 3A is a longitudinal sectional view of an example with one near-infrared LED (or red LED) and one camera module according to the first embodiment.

FIG. 3B is a longitudinal sectional view of a first modification with a plurality of near-infrared LEDs (or red LEDs) and a plurality of camera modules according to the first embodiment.

FIG. 7A is a longitudinal sectional view illustrating a relative position of the finger and the blood flow authentication ring when a person with relatively thick fingers wears the present blood flow authentication ring according to the first embodiment.

FIG. 7B is a longitudinal sectional view illustrating a relative position of the finger and the blood flow authentication ring when a person with relatively thin fingers wears the present blood flow authentication ring according to the first embodiment.

FIG. 8 is a diagram illustrating authentication determination according to the first embodiment.

FIG. 9 is a perspective view illustrating door unlocking and locking according to the first embodiment.

FIG. 13 is a flowchart from insertion of a finger to payment processing by the blood flow authentication ring according to the invention in the subject application.

DESCRIPTION OF EMBODIMENTS

A blood flow authentication ring according to embodiments of the present invention will be described in detail below with reference to the drawings. However, the embodiments described below are examples of the blood flow authentication ring to embody the technical concept of the present invention. The present invention is not limited to them and can be equally applied to other embodiments encompassed in the claims. In the embodiments of the present invention, a blood flow authentication ring to be worn on a finger is illustrated by way of example, but this is only an example. The blood flow authentication ring of the embodiments is not limited to finger-worn use, and can be applied to any body part as long as blood flow can be recognized.

First Embodiment

An illumination device according to a first embodiment of the present invention will be described with reference to FIGS. 1 to 10.

Figure 1:
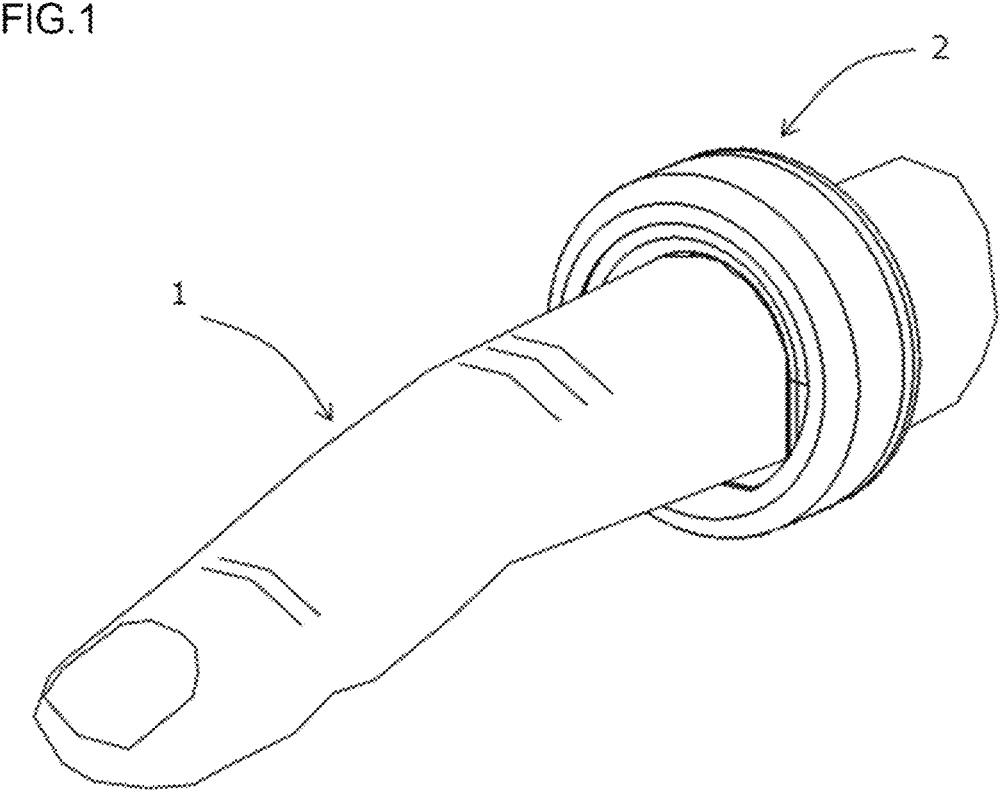
FIG. 1 is a perspective view of a blood flow authentication ring according to a first embodiment.
Figure 2:
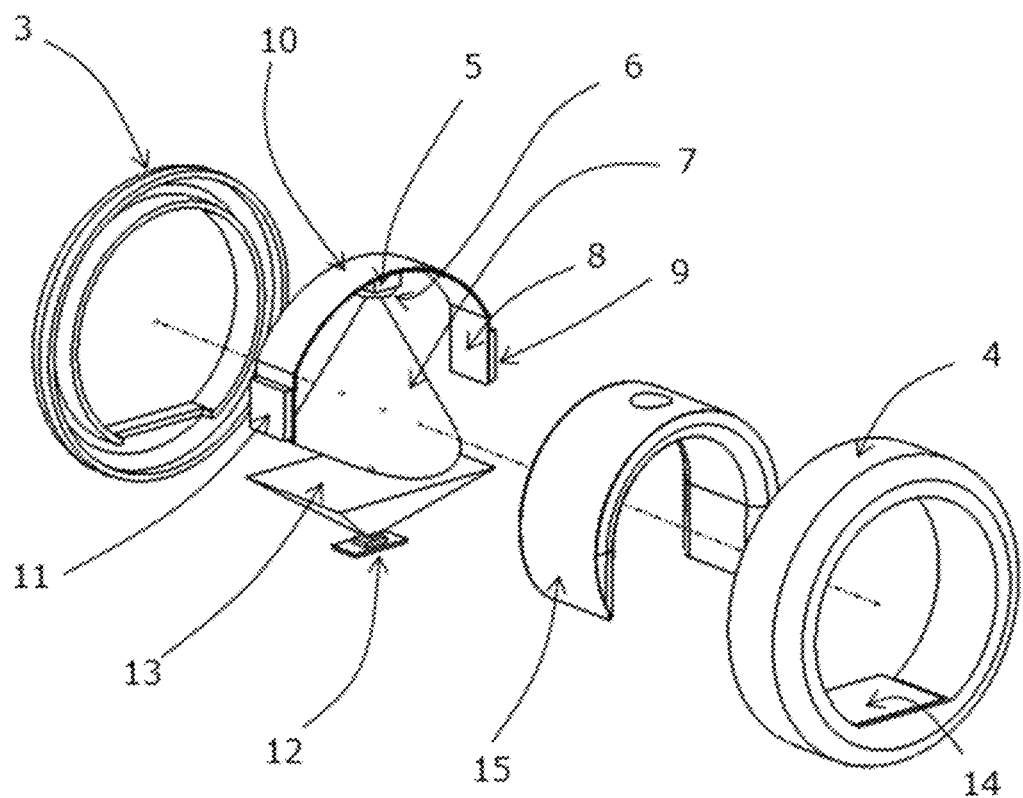
FIG. 2 is an exploded perspective view of the blood flow authentication ring according to the first embodiment.
Figure 4:
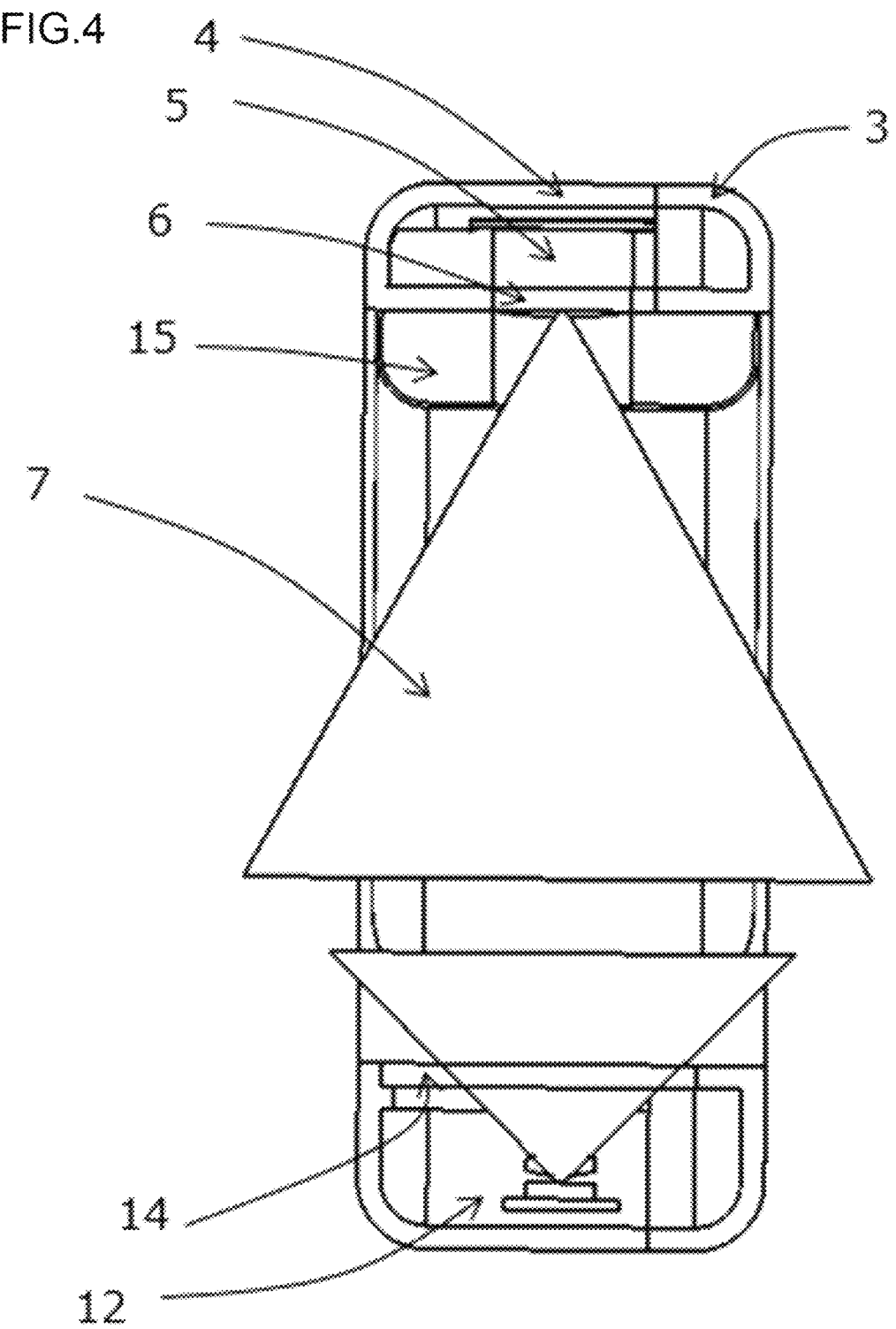
FIG. 4 is a longitudinal sectional view of another cut illustrating the first embodiment of the invention in the subject application.

FIG. 1 is a perspective view of the present embodiment. In this figure, a person who owns a blood flow authentication ring 2 is wearing the blood flow authentication ring on his or her finger. FIG. 2 is an exploded view of the present embodiment. FIG. 3A and FIG. 3B are longitudinal sectional views of the present embodiment. FIG. 4 is a longitudinal sectional view of the present embodiment.

A configuration illustrated in FIGS. 1 to 4 will now be described. The blood flow authentication ring 2 includes two cases, i.e., front and back cases, to form its exterior. The two cases are a first case 3 and a second case 4. The first case 3 and the second case 4 are secured to each other, for example, by adhesive, laser welding, or screwing. An LED 5 serving as a "near-infrared light emitter" is, for example, a near-infrared LED that emits near-infrared light of 850 nm to 950 nm or a red LED that emits red light of 600 nm to 700 nm.

FIG. 3A is a longitudinal sectional view of an example with one LED 5 (near-infrared LED or red LED) and one camera module 12 according to the present embodiment. The blood flow authentication ring 2 according to the present embodiment is an embodiment with one LED 5 (near-infrared LED or red LED).

FIG. 3B is a longitudinal sectional view of an example with a plurality of LEDs 5 (near-infrared LEDs or red LEDs) and a plurality of camera modules 12 according to a first modification of the present embodiment. The first modification is an example in which a plurality of LEDs 5 (near-infrared LEDs or red LEDs) are disposed to increase the quantity of light and expand the irradiation range. When red LEDs are used, red wavelengths as well as near-infrared wavelengths are easily absorbed by blood flow. It is possible to capture a blood flow image using transmitted light from the LEDs 5 with either wavelength, i.e., near-infrared LEDs or red LEDs.

LEDs 5 with the same specifications may be used, or LEDs 5 with different specifications may be used. For example, LEDs 5 only one of which emits a different wavelength may be used, or LEDs 5 with two or more different wavelengths may be used. For example, at least one of LEDs 5a to 5e can be changed to a red LED, and the red LED can be combined with near-infrared LEDs to obtain a clearer blood flow image.

Cover glasses 6 and 6a to 6e seal an opening in the cover and allow the irradiation light from the LEDs 5 (which hereinafter may be referred to as "near-infrared light") to pass through. An irradiation light beam 7 of the near-infrared light irradiates a range that covers the width of the finger from the back side of the finger. A flexible printed circuit board (FPC) 8 is populated with circuit components of the blood flow authentication ring 2. A microcomputer 9 performs various arithmetic operations from the obtained images. A flexible solar panel 10 supplies power to circuitry while storing power in a not-illustrated capacitor, providing a blood flow authentication ring that does not require a battery. Needless to say, it is also possible to eliminate the solar panel by supplying and charging power from an external source. A communication module 11 is, for example, a Bluetooth Low Energy (BLE) module, which has a function to pair with an external device and communicate information with low power consumption.

Camera modules 12 and 12a to 12c each include a substrate with an image sensor and a lens unit and can capture an image from the ball side of the finger. The camera modules 12 are disposed at a location where they can capture an image of the irradiation light from the LED(s) 5. For example, they can be disposed along the first case 3 and the second case 4 on the same circumference. FIG. 3A illustrates an embodiment in which one camera module is disposed. As illustrated in FIG. 3B, the first modification is an example in which the quantity of light is increased by disposing a plurality of LEDs 5 (near-infrared LEDs or red LEDs) to expand the irradiation range, and a plurality of camera modules 12 are provided. FIG. 3B illustrates an example with five LEDs 5 and three camera modules 12, but the present modification is not limited to this. The number of LEDs 5 and the number of camera modules 12 can be any number equal to or more than one as long as the camera module(s) 12 can capture an image of the irradiation light from the LED(s) 5, and they can be arranged as desired.

A light beam 13 is a light beam in the imaging range (angle of view) of the present camera module. An optical filter 14 can be, for example, a visible light cut filter having a function of cutting off 90% or more of light with wavelengths lower than a range of 850 nm to 950 nm. When a visible light cut filter is used as the optical filter, images of wrinkles, scratches, and the like on the surface of the finger that are not necessary for blood flow authentication are not captured, thereby increasing the accuracy of blood flow authentication. A size compensation member 15 is a member interposed between the finger and the ring.

The LED 5, the communication module 11, and the microcomputer 9 are mounted on the FPC 8. The first case 3 has a circumferential recessed groove. The FPC 8 is secured between the first case 3 and the second case 4 in the form of an arc that conforms to the recessed groove. The second case 4 has a circumferential recessed groove in the same manner as in the first case 3. The second case 4 has an opening on the inner circumference side of the LED 5 so that the irradiation light from the LED 5 can pass through at the arrangement position of the LED 5. The camera module 12 is stored in a camera module housing in the recessed groove of the second case 4. Since the optical filter 14 is provided on the inner circumference side of the camera module housing, an image of the irradiation light (irradiation light beam 7) from the LED 5 is captured as the camera light beam 13 by the camera module 12 through the optical filter 14.

The size compensation member 15 is a substantially U-shaped member along the arc shape, is disposed on the inner circumference side of the first case 3 and the second case 4, and functions as a spacer between the inner circumference of the first case 3 and the second case 4 and the outer circumference of the finger. A through hole is provided at a portion of the size compensation member 15 corresponding to the arrangement position of the LED 5. The irradiation light (irradiation light beam 7) from the LED 5 passes through the through hole and irradiates the inner circumference side of the size compensation member 15.

Figure 5:
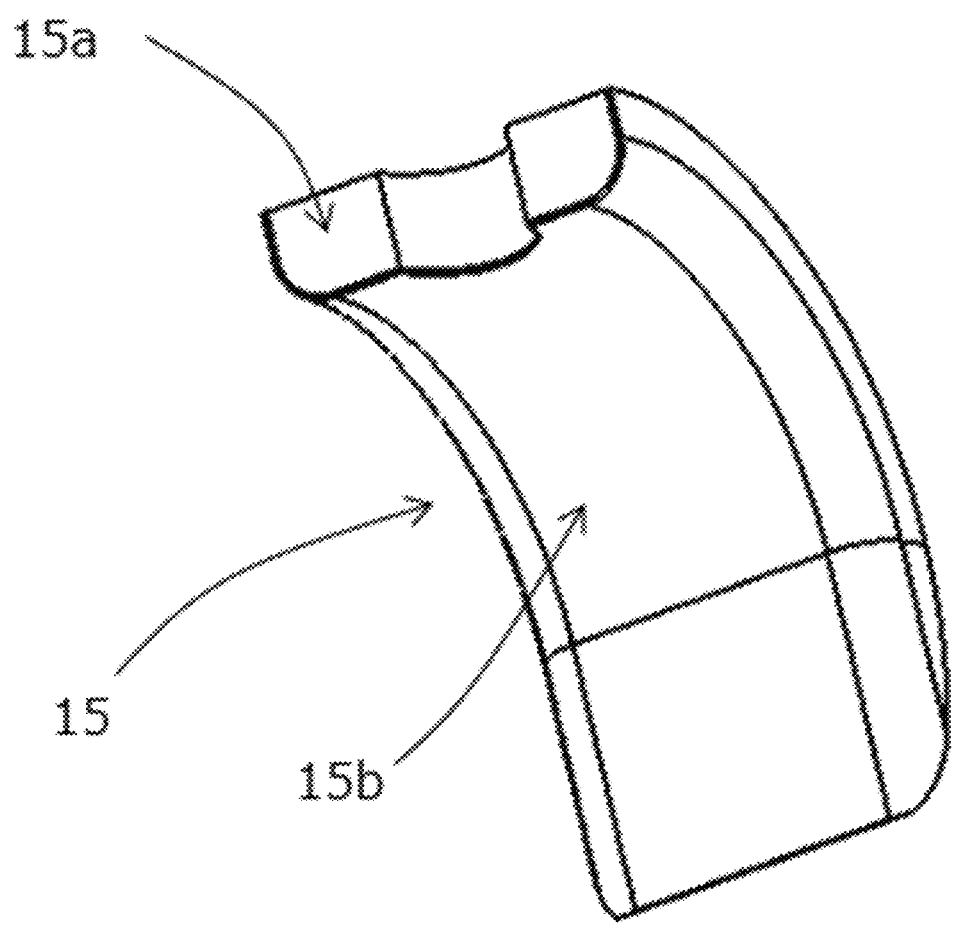
FIG. 5 is a diagram illustrating a structure of a size compensation member according to the invention in the subject application.

FIG. 5 is a diagram illustrating a structure of the size compensation member 15 according to the invention in the subject application. The size compensation member 15 includes an elastic member 15a and a surface member 15b. The elastic member 15a is a member having elasticity. The surface member 15b is a sheet-like material with a reflectivity of less than 10% for 850 nm to 950 nm and is formed integrally with the elastic member. The surface member 15b is a material having a surface with a coefficient of kinetic friction of less than 0.2 and is surface-treated to minimize snagging during finger insertion and to enable smooth insertion and removal. Furthermore, increasing the slidability of the surface of the surface member 15b enhances the durability against repeated insertion and removal.

Figure 6:
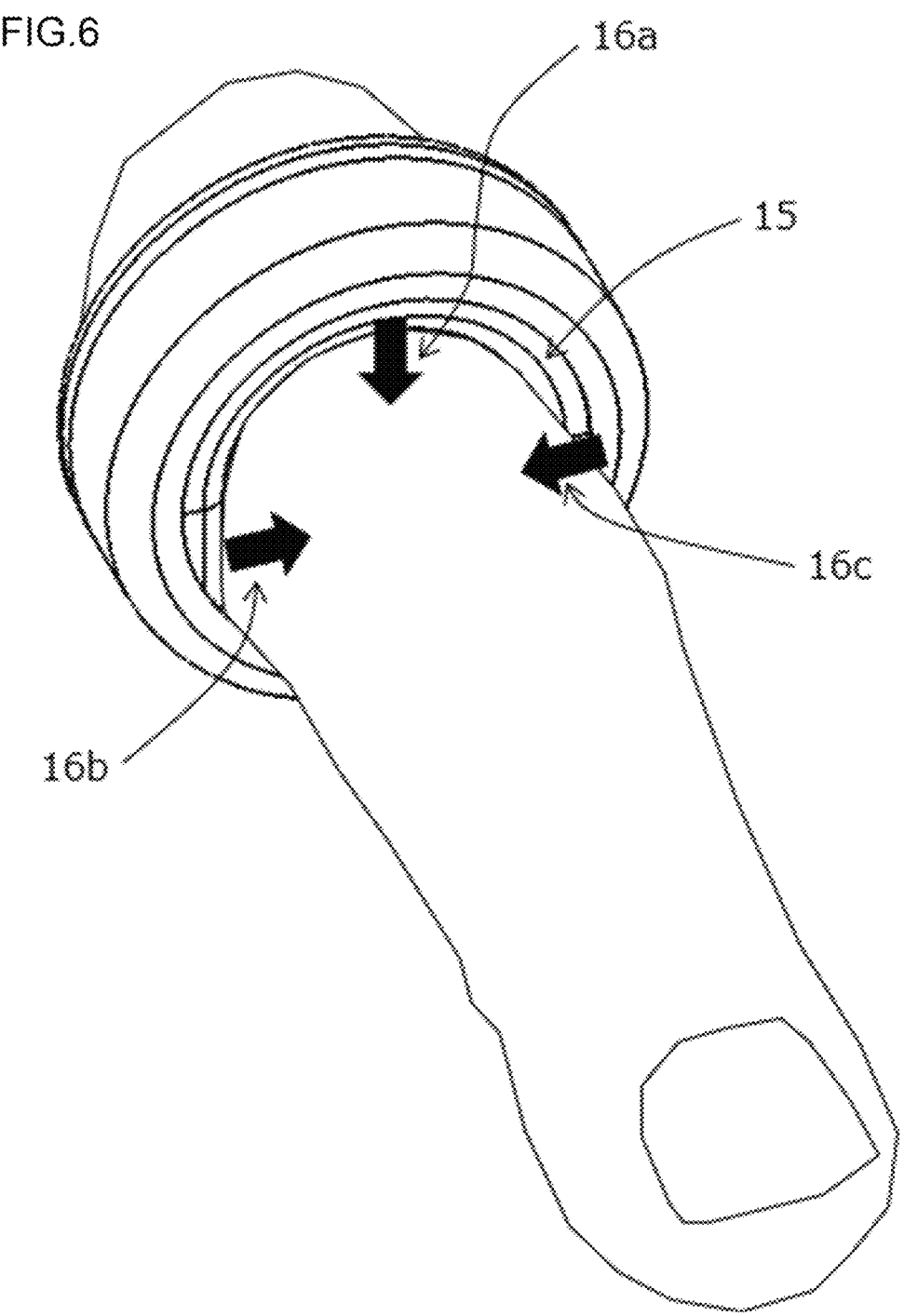
FIG. 6 is a diagram illustrating directions of force exerted by deformation of the size compensation member according to the invention in the subject application.

FIG. 6 is a diagram illustrating directions of force exerted by deformation of the size compensation member 15 according to the invention in the subject application. The size compensation member 15 supports at least the upper (back) side of the finger and both side surfaces of the finger. When the ring is worn, elastic force is exerted in the directions indicated by arrows 16a, 16b, and 16c in FIG. 6 to bias the finger toward the center of the ring in the lateral direction and downward (toward the camera module) in the vertical direction.

FIG. 7A is a longitudinal sectional view illustrating a relative position of a finger 1 and the blood flow authentication ring 2 when a person with relatively thick fingers wears the present blood flow authentication ring 2 according to the invention in the subject application. FIG. 7B is a longitudinal sectional view illustrating a relative position of the finger 1 and the blood flow authentication ring 2 when a person with relatively thin fingers wears the present blood flow authentication ring 2 according to the invention in the subject application.

In FIG. 7A, a relatively thick finger is inserted into the blood flow authentication ring 2, causing the size compensation member 15 to deform from the inner circumference side toward the outer circumference by an amount of deformation 17a. In FIG. 7B, a relatively thin finger is inserted into the blood flow authentication ring 2, causing the size compensation member 15 to deform from the inner circumference side toward the outer circumference by an amount of deformation 17b. In this case, the amount of deformation 17a is larger than the amount of deformation 17b, according to the thickness of the finger. In this way, as illustrated in FIGS. 7A and 7B, the size compensation member 15 has the amounts of deformation 17a and 17b changing according to the thickness of the finger, so that the elasticity of the size compensation member 15 enables the ring to be worn with no gap while absorbing the difference in the thickness of the finger, and biases the finger downward (toward the camera module). As a result, a distance X from the imaging position of the camera module 12 (focus plane, image formation position in FIGS. 7A and 7B) to the surface of the finger 1 is kept constant regardless of the size of the finger.

Although finger blood vessels exist inside the finger, the image irradiated by near-infrared light is once projected near the surface of the finger, and the projected image is captured. Therefore, the constant distance X from the imaging position (focus plane, image formation position in FIGS. 7A and 7B) to the surface of the finger is advantageous in that a stable in-focus image can be obtained regardless of the human finger thickness. In the invention in the subject application, the surface member 15b is a sheet-like material with a reflectivity of less than 10% for 850 nm to 950 nm. Since the size compensation member 15 has a surface with low reflectivity, the reflection on the ring inner circumference side due to stray light caused by near-infrared light irradiation or external light is also suppressed, resulting in a blood flow image with high contrast. Needless to say, in a case where there is no size compensation member, the same effect can be achieved by applying the same low-reflectivity treatment to the inside of an enclosure.

FIG. 8 is a diagram illustrating authentication determination according to the invention in the subject application. The owner of the blood flow authentication ring 2 registers himself or herself to be authenticated in advance before performing blood flow authentication (registered image: 18). Blood flow captured images 19a, 19b, 19c, 19d, and 19e are images of different human fingers. The present blood flow authentication ring compares a blood flow authentication image with the registered image 18 acquired in advance and determines whether the person wearing the ring is the owner based on the fact that 19a to 19d are different from the owner's blood flow and only 19e is identical to the registered image.

FIG. 9 is a perspective view of door unlocking and locking with the blood flow authentication ring 2 according to the present embodiment. A receiving unit 20 can receive a BLE signal as a communication signal, a unit 21 unlocks and locks the door, and a door knob 22 opens and closes the door. Communication 23 is, for example, BLE communication.

Figure 10:
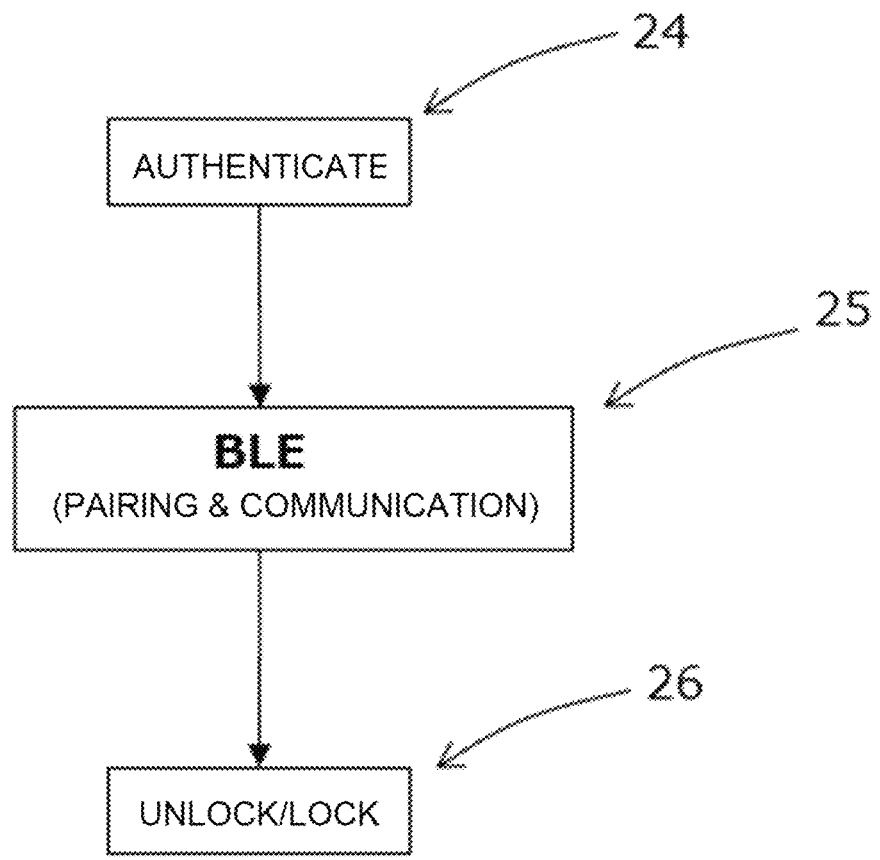
FIG. 10 is a flowchart illustrating the door unlocking and locking according to the first embodiment.

FIG. 10 is a flowchart illustrating door unlocking and locking with the blood flow authentication ring according to the invention in the subject application. If the registered image described earlier and the captured image match and authentication is established (authenticated) (24 in the flowchart), pairing and information communication are performed between the present blood flow authentication ring 2 and the receiving unit 20 installed at the door (25 in the flowchart). If an authentication signal is received by the receiving unit 20 at the door, a door unlocking signal is sent to the door unlocking/locking unit 21 to unlock the door (26 in the flowchart). Subsequently, the door to the interior is automatically locked after a predetermined period of time after the door was closed.

The blood flow authentication result by the blood flow authentication ring 2 is transmitted to the receiving unit 20 through the communication module 11 via the communication 23, for example, BLE communication. As a result, if the blood flow authentication result indicates authenticated, the unlocking/locking operation of the door lock 21 is enabled. On the other hand, if the blood flow authentication result indicates unauthenticated, the unlocking/locking operation of the door lock 21 is disabled. With this configuration, only when the blood flow authentication result from the blood flow authentication ring 2 indicates authenticated and proper communication is established from the blood flow authentication ring 2, the unlocking/locking operation of the door lock 21 is enabled in a contactless manner via the communication 23, even without using a mechanical key.

For example, if the blood flow authentication ring 2 is lost or stolen and someone else tries the unlocking/locking operation of the door lock 21 using the blood flow authentication ring 2, the blood flow authentication result indicates unauthenticated with another person's finger. Thus, it is impossible for another person to perform the unlocking/locking operation of the door lock 21 in a contactless manner using the blood flow authentication ring 2.

Second Embodiment

Figure 11:
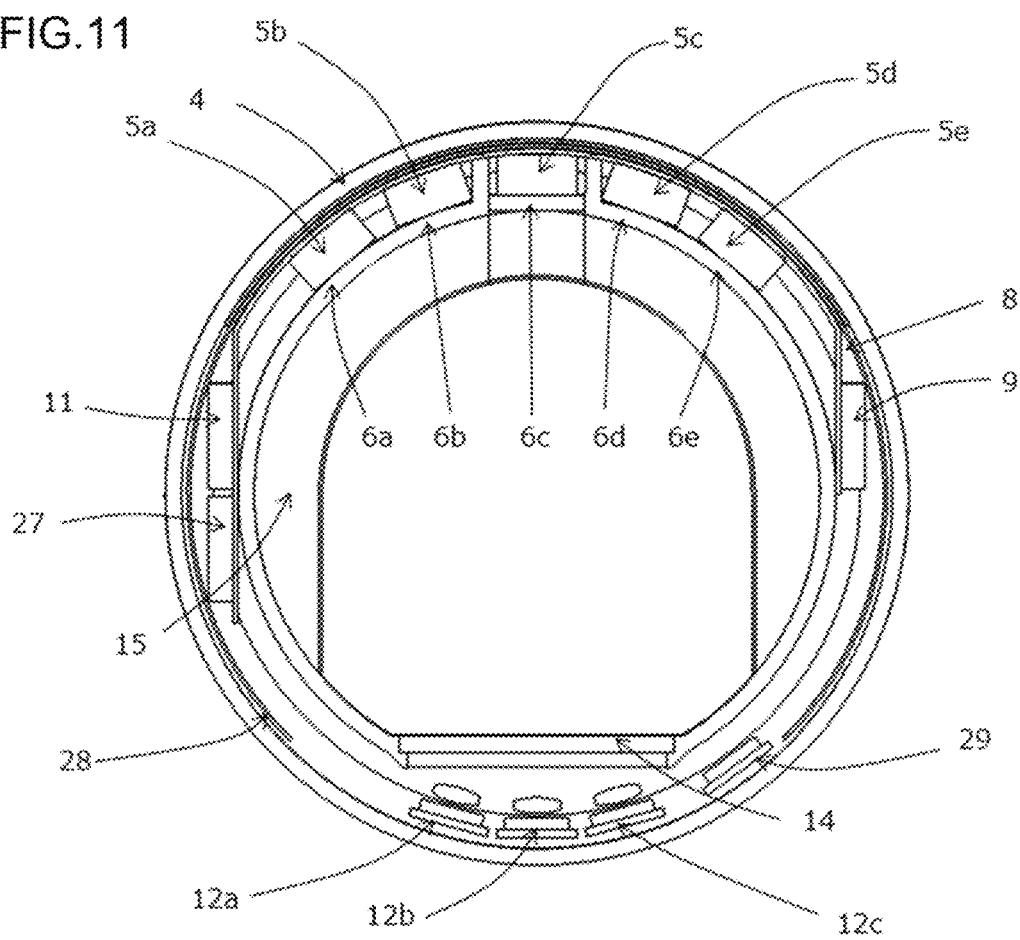
FIG. 11 is a longitudinal sectional view with a vital sensor and NFC added according to a second embodiment.

The blood flow authentication ring according to a second embodiment of the present invention will be described with reference to FIGS. 11 and 12. The same configuration as in FIGS. 1 to 10 is denoted by the same reference sign and will not be further elaborated. FIG. 11 is a longitudinal sectional view with a vital sensor and NFC added according to the second embodiment.

The blood flow authentication ring 2 according to the present embodiment includes a small reflective sensor (hereinafter referred to as "vital sensor") 29 that incorporates red and infrared LEDs and a highly sensitive photodiode that receives the reflected light in a single package, a near field communication device (hereinafter referred to as "NFC") 27, and a flexible antenna (flexible circuit board with antenna) 28. The vital sensor 29 can be used to measure blood oxygen saturation (hereafter referred to as SpO2 value) from the ratio (R/IR) of varying components of the transmitted light quantity of red light (R) and infrared light (IR). In addition, by observing the pulsation (varying component), the component of arterial blood alone can be observed, and by observing this variation, the pulse rate can also be determined at the same time. The interval between beats of the pulse fluctuates slightly, and the degree of fluctuations of the pulse is considered as "stress level". The greater the fluctuations of the pulse, the lower the stress level, and the smaller the fluctuations of the heart rate, that is, constant intervals, the higher the stress level. Furthermore, it is known from experiments that there is a correlation between blood pressure and acceleration plethysmogram obtained by the second derivative of the pulse rate, so the blood pressure can be estimated. In this way, the vital sensor can be used to measure SpO2 value, pulse rate, stress level, and estimated blood pressure.

NFC described above stands for "near field communication" meaning short-range wireless communication, which is a technology and a payment method that enable communication simply by waving a contactless IC chip. NFC is used for smartphones and prepaid cards. In recent years, NFC-equipped credit cards and smart rings for payment have appeared on the market, simplifying payments. On the other hand, there is a risk of losing such devices or cards, resulting in someone else using them for payment. The present device has a great advantage of preventing payment by anyone other than the user himself/herself because the ring activates the NFC function only when personal authentication is established. Since contactless IC chips are embedded in relatively flat surfaces in cards, smartphones, and the like, the users can enable communication with relatively high sensitivity even in close proximity by waving the flat surfaces where the IC chips are embedded. On the other hand, smart rings have few flat areas and vary in communication sensitivity when waved, making it difficult to respond. In the present device, the flexible antenna 28 for NFC is disposed in a wide section inside the ring surface separately from the NFC 27, which is a contactless IC, to increase communication sensitivity and to make the ring more responsive in various ways of waving.

Figure 12:
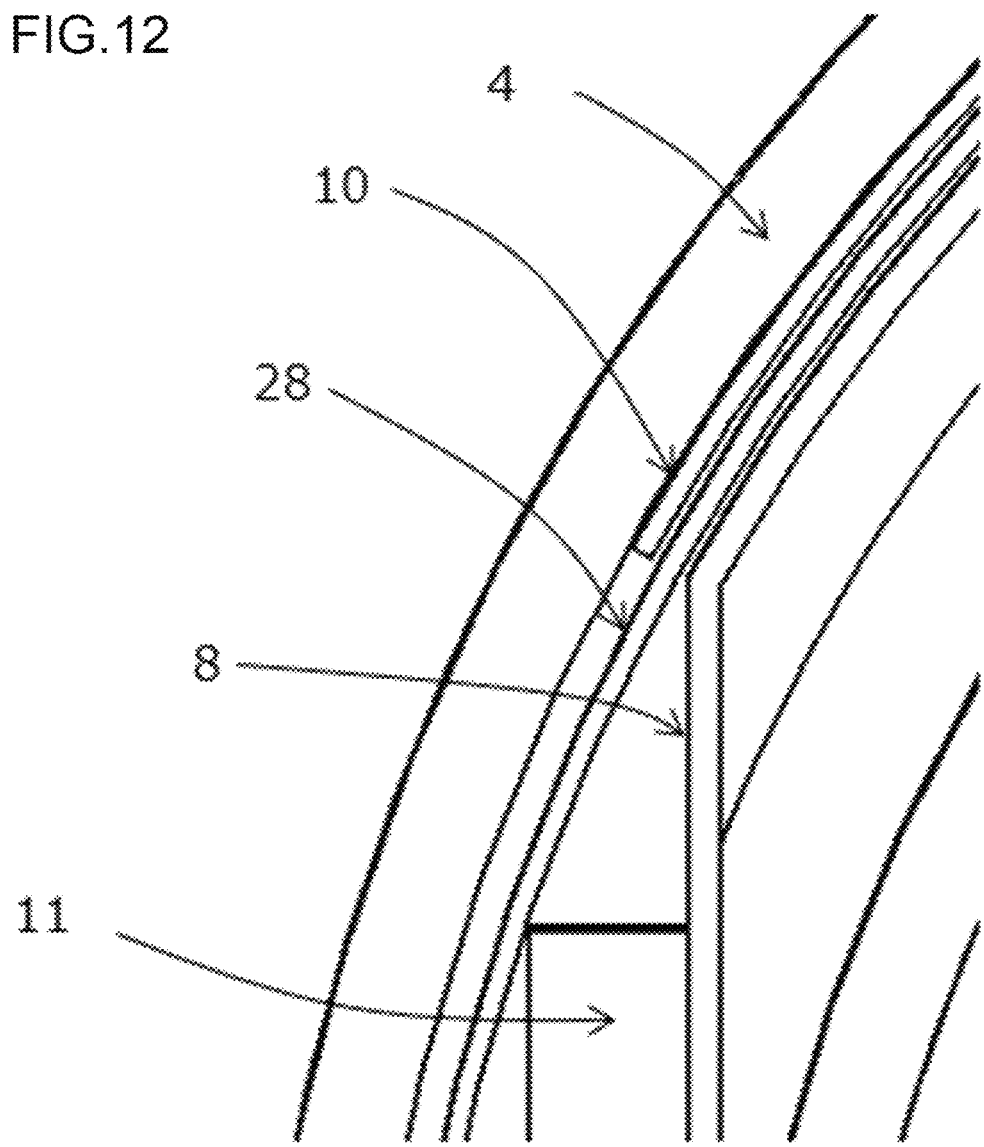
FIG. 12 is an enlarged view of the arrangement relationship between a flexible antenna for NFC and a solar panel, in the invention according to the subject application.

FIG. 12 is an enlarged view of the arrangement relationship between the flexible antenna 28 for NFC and the solar panel 10. The solar panel 10 is disposed on the outermost surface inside the first case 4, and the flexible antenna 28 for NFC is disposed on the back side of the solar panel 10. In this configuration, the solar panel 10 can maximize light-receiving efficiency without being blocked. On the other hand, since the solar panel 10 is not magnetic, disposing the flexible antenna 28 for NFC on the back side does not interfere with NFC communication sensitivity.

FIG. 13 is a flowchart from insertion of a finger to payment processing by the blood flow authentication ring 2 according to the present embodiment. The precondition is that the blood flow authentication ring 2 has an identification number printed and written for each blood flow authentication ring 2 during a manufacturing process, and a payment system is finally activated (validated) corresponding to the identification number of the blood flow authentication ring 2. To prevent anyone else from being able to make a payment based on the identification number of the blood flow authentication ring 2, the owner of the blood flow authentication ring 2 must register himself/herself in advance before performing blood flow authentication, as described above. The blood flow authentication ring 2 activates the vital sensor at regular intervals to detect the wearing/not wearing of the ring (30 in the flowchart). If it is detected that the ring in a not-wearing state is worn and it is determined that the wearing is for the first time (31 in the flowchart), personal registration is automatically performed (32 in the flowchart). With the ring still worn, the NFC function is activated (34 in the flowchart), and payment processing is enabled (36 in the flowchart). Once the blood flow authentication ring 2 is removed from the finger, the authentication status of the ring is reset based on the detection of wearing/not wearing as described above. If the wearing state is detected again and it is determined that the wearing is for the second or subsequent time, the authentication flow is entered (24 in the flowchart). The blood flow authentication ring 2 compares the blood flow authentication image with the registered image acquired in advance as described above, and determines whether the person wearing the ring is the owner based on the fact that the image is identical to the registered image (33 in the flowchart). If the person is determined as the owner, the NFC function is activated; If not, the NFC function is inactivated (34, 35 in the flowchart). With the NFC function activated, payment processing is performed (36 in the flowchart).

While the blood flow authentication ring 2 according to the embodiments of the present invention has been described above, the foregoing embodiments are examples of the blood flow authentication ring 2 to embody the technical concept of the invention. The present invention is not limited to them and can be equally applied to other embodiments, such as modifications of each embodiment or combinations of embodiments.

In the embodiments of the present invention, a blood flow authentication ring to be worn on a finger is illustrated by way of example, but this is only an example. The blood flow authentication ring of the embodiments is not limited to finger-worn use, and can be applied to any body part as long as blood flow can be recognized. For example, it can be applied to arms, legs, face (e.g., ears), and the like.

The flowchart for personal authentication is only an example, and various other procedures and flowcharts are applied in the embodiments of the present invention.

The structure and shape of the blood flow authentication ring 2 illustrated in the embodiments are examples only. The structure and shape of the embodiments are not limited thereto, and there is a wide range of design freedom such as design, assembly, and selection of parts.

INDUSTRIAL APPLICABILITY

The size compensation member disposed on the inner circumference side of the blood flow authentication ring 2 can make a constant distance from an image pickup element to the finger surface even if the finger size varies, providing industrial applicability. In addition, the ring that has a blood flow authentication function, a payment function, and a vital information acquisition function enables the users to perform personal registration to authentication in an easy way, and thus is easy for anyone to use and is secure, providing industrial applicability.

The invention claimed is:

1. A blood flow authentication ring configured to perform authentication with finger blood flow, the blood flow authentication ring comprising:
a ring-shaped cover member to be worn on a finger, wherein
the cover member at least comprises
an irradiation circuitry configured to irradiate the finger with light, and
an imaging circuitry configured to capture an image of light transmitted through the finger,
the irradiation circuitry is opposite the imaging circuitry and is placed on the back side of the finger,
an adjusting member is provided between an inner circumference of the cover member and the finger,
the adjusting member has a function of a low reflection member,
the adjusting member is disposed at least between an inner circumference side of the cover member, and the back side and both side surfaces of the finger, and
the low reflection member has a reflectivity of less than 10%.

2. The blood flow authentication ring according to claim 1, wherein the adjusting member has a surface with a coefficient of kinetic friction of less than 0.2.

3. The blood flow authentication ring according to claim 1, wherein the cover member has a solar panel.

4. The blood flow authentication ring according to claim 1, wherein light emitted by the irradiation circuitry is at least one of near-infrared light and red light.

5. The blood flow authentication ring according to claim 1, wherein the adjusting member is an elastic member.

6. The blood flow authentication ring according to claim 1, wherein the adjusting member has a light-transmitting portion that allows light emitted from the irradiation circuitry to pass through.

7. The blood flow authentication ring according to claim 1, wherein at least one of the irradiation circuitry and the imaging circuitry is provided in plurality.

8. A blood flow authentication ring configured to perform authentication with finger blood flow, the blood flow authentication ring comprising:
a ring-shaped cover member to be worn on a finger, wherein
the cover member at least comprises
an irradiation circuitry configured to irradiate the finger with light, and
an imaging circuitry configured to capture an image of light transmitted through the finger,
the irradiation circuitry is opposite the imaging circuitry and is placed on the back side of the finger,
an adjusting member is provided between an inner circumference of the cover member and the finger,
the adjusting member has a function of a low reflection member,
the adjusting member is disposed at least between an inner circumference side of the cover member, and the back side and both side surfaces of the finger, and
the low reflection member has a reflectivity of less than 10%
the cover member further comprises a finger detector configured to detect wearing on the finger, and
the finger detector has a registration function to automatically register a person, to be authenticated, corresponding to the finger when the finger detector detects wearing on the finger for a first time.

* * * * *